(12) United States Patent
Raupach et al.

(10) Patent No.: US 8,675,937 B2
(45) Date of Patent: Mar. 18, 2014

(54) METHOD FOR INCREASING THE QUALITY OF COMPUTER TOMOGRAPHIC RECORDING SERIES BY PROJECTION DATA PROCESSING AND CT SYSTEM HAVING A COMPUTATION UNIT

(75) Inventors: Rainer Raupach, Heroldsbach (DE); Anja Borsdorf, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 561 days.

(21) Appl. No.: 12/314,892

(22) Filed: Dec. 18, 2008

(65) Prior Publication Data

US 2009/0161820 A1 Jun. 25, 2009

Related U.S. Application Data

(63) Continuation-in-part of application No. 11/703,243, filed on Feb. 7, 2007, now abandoned.

(30) Foreign Application Priority Data

Feb. 8, 2006 (DE) .......................... 10 2006 005 803
Dec. 21, 2007 (DE) .......................... 10 2007 061 934

(51) Int. Cl.
*A61B 6/03* (2006.01)

(52) U.S. Cl.
CPC ........................................ *A61B 6/03* (2013.01)
USPC ........................................................ 382/131

(58) Field of Classification Search
USPC .................................... 378/4; 382/128–132
See application file for complete search history.

(56) References Cited

U.S. PATENT DOCUMENTS 4,463,375 A * 7/1984 Macovski .................. 378/98.12
6,178,223 B1 * 1/2001 Solomon et al. ................ 378/62

(Continued)

FOREIGN PATENT DOCUMENTS

DE 10 2005 12 654 10/2006
DE 102005012654 A1 10/2006

(Continued)

OTHER PUBLICATIONS

Bruder et al., Design considerations in cardiac CT, Feb. 2006, SPIE, vol. 6142, pp. 61420H-1 to 61420H-13.*

(Continued)

*Primary Examiner* — Toan Ton
*Assistant Examiner* — John Corbett
(74) *Attorney, Agent, or Firm* — Harness, Dickey & Pierce, P.L.C.

(57) ABSTRACT

A method is disclosed for increasing the quality of computer tomographic recording series, to a computation unit and to an X-ray CT system. An embodiment of the method includes scanning a subject over a period of time which makes it possible to record at least two temporally offset projection data sets of the same recording region; transforming the projection data sets into transformation data sets for at least two spatial frequency ranges; calculating temporal compensation values of the transformation data sets for some of the spatial frequency ranges and replacing the compensated values of the transformation data sets with the calculated compensation values in new transformation data sets, projection data of congruent rays always being compared; transforming the new transformation data sets back into new projection data sets; reconstructing image data sets on the basis of the new projection data sets and representing the image data sets.

18 Claims, 5 Drawing Sheets

(56) References Cited

U.S. PATENT DOCUMENTS

| | | | |
|---|---|---|---|
| 2006/0235293 A1 | 10/2006 | Raupach et al. | |
| 2007/0040831 A1 | 2/2007 | Flohr et al. | |
| 2007/0053477 A1* | 3/2007 | Ning | 378/4 |
| 2007/0189635 A1* | 8/2007 | Borsdorf et al. | 382/275 |
| 2008/0221442 A1* | 9/2008 | Tolkowsky et al. | 600/425 |
| 2009/0034818 A1* | 2/2009 | Morita | 382/131 |

FOREIGN PATENT DOCUMENTS

| | | |
|---|---|---|
| DE | 10 2005 038 940 | 3/2007 |
| DE | 102005038940 A1 | 3/2007 |
| DE | 102006005803 A1 | 8/2007 |

OTHER PUBLICATIONS

Schreiber Translations, Inc., Jun. 2011, PTO 11-4542, English translation of DE10305221, 25 Pages plus cover.*

Chen et al., Cone-beam CT breast imaging: wavelet analysis-based multi-resolution reconstruction and de-noising technique, 2002, SPIE, vol. 4682, pp. 236-244.*

Perona et al. "Scale-space and edge detection using anisotropic diffusion", IEEE Transactions on Pattern Analalysis and Machine Intelligence, vol. 12, pp. 629-639, 1990; Others; 1990.

J. Weickert, "Anisotropic Diffusion in Image Processing", Teubner-Vertag, Stuttgart, Germany, 1998, pp. 95-105; Book.

Proc. SPIE, Olsen, E.T.; Lin, B.; vol. 2491. Seite 829-839; Others; 1995.

Peyrin. F.; Zaire, M.; Goutte, R., IEEE Proc. Engineering in Medicine and Biology Society, vol. 1, 1994, Seite 4a-5a; Others; 1994.

Office Action dated Nov. 27, 2008 for corresponding German Patent Application No. 10 2007 061 934.2 with English translation.

* cited by examiner

FIG 6
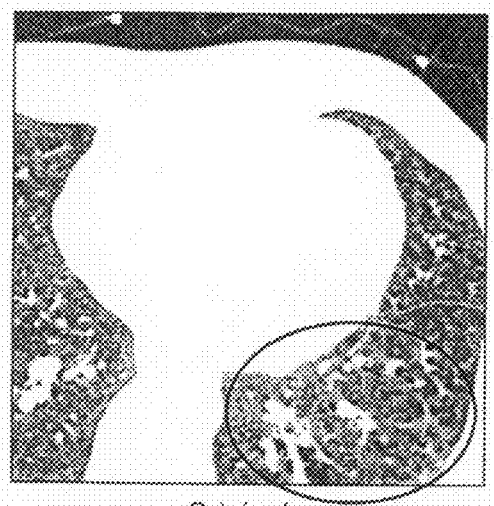
Original
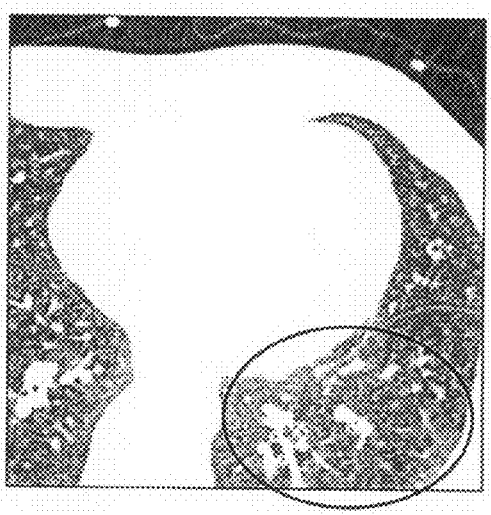
Filtered
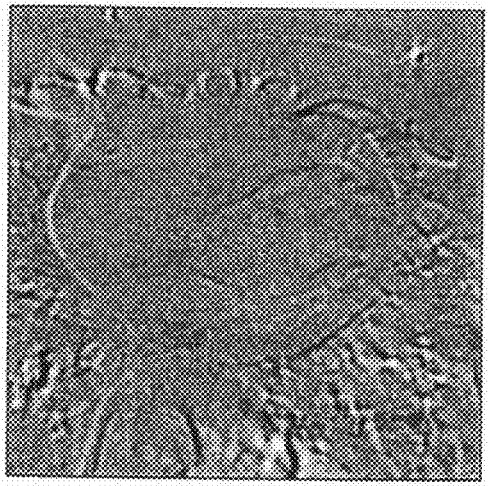
Difference: Filtered minus Original
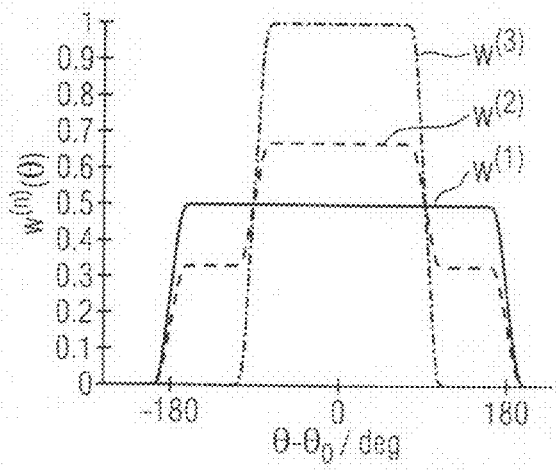
Filtered Functions

US 8,675,937 B2

METHOD FOR INCREASING THE QUALITY OF COMPUTER TOMOGRAPHIC RECORDING SERIES BY PROJECTION DATA PROCESSING AND CT SYSTEM HAVING A COMPUTATION UNIT

PRIORITY STATEMENT

The present application hereby claims priority under 35 U.S.C. §119 on German patent application number DE 10 2007 061 934.2 filed Dec. 21, 2007, the entire contents of which is hereby incorporated herein by reference. Further, this application claims priority under 35 U.S.C. §120 to, and is a continuation-in-part of, U.S. patent application Ser. No. 11/703,243, filed Feb. 7, 2007, which claims the benefit of German Patent Application No. 10 2006 005 803.8, filed Feb. 8, 2006.

FIELD

Embodiments of the invention generally relate to a method for increasing the quality of computer tomographic recording series by projection data processing, a multiplicity of chronologically successive projection data sets being recorded by a CT system as a recording sequence, and optionally reconstructed, and these projection data sets being improved by electronic filtering and post-processing.

BACKGROUND

In order to increase the quality of computer tomographic recording series, it is known to process image data sets that have already been reconstructed. The document DE 10 2005 038 940 A1 may for example be cited, in which an edge-preserving filter is used for image enhancement of the reconstructed image data sets. In the publication P. Perona and J. Malik, Scale space and edge detection using anisotropic diffusion, IEEE Transactions on Pattern Analysis and Machine Intelligence, Vol. 12, pp. 629-639, 1990; J. Weichert, Anisotropic Diffusion Filtering in Image Processing, Teubner-Verlag, Stuttgart, Germany, 1998, diffusion filters are applied to reconstructed image data in order to improve the image quality. The document DE 10 2005 012 654 A1 may furthermore be cited, in which image data are filtered by using correlation calculations, here again in order to produce a quality improvement.

However, all these known methods for increasing the quality of computer image recordings by image data processing reach their limitations when the relevant contrast is close to or less than the noise. If CT perfusion scans of particular organs are considered, for example the brain, liver or heart, then it is found that the typical CT value changes which are needed in order to detect the perfusion lie in the range of about 2 to 20 HU, i.e. 0.2 to 2% of the contrast of water against air. The pixel noise therefore plays a crucial role.

Another problem is that each of the methods requires reconstruction of the image data sets before the data material is processed, which entails a relatively high computation cost.

SUMMARY

In at least one embodiment of the invention, a method is provided for increasing the quality of computer tomographic recording series which makes it possible to reduce the noise greatly, without compromising the detail structure or the time resolution in the image. On the other hand, in at least one embodiment, a reduction of the computation cost is also intended to be achieved in relation to processing at the image data set level.

In a CT perfusion scan, the blood supply is determined with measurement values for the blood volume, time to peak, etc. of a particular organ, for example the brain or the liver. In many cases, the functional information provides a significant gain over a CT angiography since not only can indirect conclusions be drawn regarding stenoses in the arteries, but also the direct effects on the tissue are visible.

In order to be able to derive the corresponding quantities from the tissue contrast measured as a function of time by the CT scan, a long scan—about 40 s—is carried out with the administration of a contrast agent. Such a long scan, however, is associated with a relatively high organ dose. Attempts are made to minimize the radiation dose used for such scans, for instance CT perfusion measurement or dynamic CT angiography (CTA). Only in this way can frequently performed scans be justified.

In these recordings, a time series of image data sets with slice recordings or volume data are calculated from continuously recorded data. By measuring the CT values, it is then possible to determine the tissue contrast as a function of time. The typical CT value change is however only about 2-20 HU, i.e. only 0.2-2% of the contrast of water against air. This applies both to measured projection data and to image data reconstructed therefrom. The pixel noise therefore also plays a crucial role.

Reducing the dose applied during the recording increases the noise in the image data, so that determination of the CT values with the required accuracy can no longer be ensured.

Reducing the noise by a linear lowpass filter, for example with a very soft convolution kernel, simultaneously degrades the spatial resolution and therefore the spatial definition of a particular area. The use of edge-preserving image filters, diffusion filters, filtering with the use of correlations or other similar techniques reach their limitations here, because the relevant contrast is close to the noise or is even less than the noise.

The Inventor has observed that the contrast change of the tissue takes place in the low spatial frequency range, while the data components with high spatial frequencies change only slowly as a function of time. The blood vessel itself is an exception to this, although its contrast change is used only to determine the blood flow and is otherwise excluded from the analysis. By correspondingly splitting the image data, it is therefore possible for noise and perfusion effects to be separated, treated separately and subsequently recombined to form new image data.

Such a procedure is proposed in a parallel application. To this end the reconstructed images are decomposed into frequency bands, each frequency band-related sub-image is differently treated or filtered, information concerning a plurality of temporally offset image data being taken into account for noise reduction, and they are subsequently recombined to form a new overall image.

A detailed description of this method at the image data set level is provided in a parallel patent application in the name of the Applicant with the same priority DE 10 2007 061 935 which corresponds to U.S. Pat. No. 8,306,303, the entire contents of each which is hereby incorporated herein by reference).

There, a prolonged scan is carried out in order to observe the perfusion profile in the tissue, from the projection data of which a chronological sequence of image data sets $I_t$ is obtained after reconstruction. These are decomposed into N frequency bands $\hat{I}_t^{(n)}$ (n=1, ..., N) with the aid of a transformation G, such that the inverse transformation $G^{-1}$ of these components again gives the corresponding image per se.

Various methods are proposed by way of example as a transformation, for example:

1) wavelet transformation, where $\hat{I}_t^{(n)}$ denotes the coefficients at the $n^{th}$ level;
2) Fourier transformation combined with frequency-dependent weight functions $F^{(n)}$ such that their sum is normalized, $$\text{i.e. } \sum_{n=1}^{N} F^{(n)} \equiv 1, \text{ and } \hat{I}_t^{(n)} = F^{(n)}(G\{I_k\});$$

3) filtering with filters for different frequencies or frequency bands.

From the components in the respective frequency bands at different times, image data sets $\tilde{I}_t$ can now be calculated with $$\tilde{I}_t = G^{-1}\left\{\sum_k a_{1,k} \hat{I}_{t+k}^{(1)}, \ldots, \sum_k a_{N,k} \hat{I}_{t+k}^{(N)}\right\}.$$

The weights $a_{n,k}$ must be normalized for each band and have a vanishing first moment.

Owing to weighted averaging over a plurality of instants in particular frequency bands, the image data set of the inverse-transformed result image $\tilde{I}_t$ has lower noise than the image data set of the original image $I_t$.

In practice, however, this method leads to two restrictions or obstacles:

The overall weight of each projection in the final image is not freely selectable; rather, it is determined to a considerable extent by the reconstruction algorithms and the timebase of the images.

If the method is applied to a gated cardio recording series in order to reduce artifacts, then very many image reconstructions are necessary compared with the number of final images. All the starting images must furthermore be decomposed into spatial frequency bands with the aid of two-dimensional filters, and inverse-transformed again. This leads to a high complexity of the method, and a large computation capacity is required.

The Inventor now proposes to apply, in at least one embodiment, the method of described above—i.e. the separating information of an image data set into different frequency bands, separate and different treatment of these image data subsets and subsequent recombination of the optionally only partially treated image data subsets to form a new image data set—even before the reconstruction, i.e. no longer to image data sets but to projection data sets.

The advantage is essentially that the method of at least one embodiment can be formulated very generally on the basis of raw data, and at the same time the computation complexity is greatly reduced.

According to this basic concept explained above, the Inventor provides a method, in at least one embodiment, for increasing the quality of computer tomographic recording series, containing the following method steps:

scanning a subject over a period of time which makes it possible to record at least two temporally offset projection data sets of the same recording region (=recording series), transforming the projection data sets into transformation data sets for at least two spatial frequency ranges, calculating temporal compensation values of the transformation data sets for some of the spatial frequency ranges and replacing the compensated values of the transformation data sets with the calculated compensation values in new transformation data sets, projection data of congruent rays always being compared, transforming the new transformation data sets back into new projection data sets, reconstructing image data sets on the basis of the new projection data sets and representing the image data sets.

In respect of the congruent rays mentioned above, it should be pointed out that these may be rays with an identical position in space, the alignment of which is not taken into account. In this sense, complementary rays may also be regarded as congruent. It is, however, also possible to compare only data of rays which are identical in position and direction. If there are no congruent data in the comparison data sets, then they may also be determined in a manner known per se by interpolation.

According to one variant of at least one embodiment of the method, a wavelet transformation is used for transforming the projection data sets, the spatial frequency ranges being determined by the level of the wavelet transformation and the compensation values being determined on the basis of the wavelets.

Another possibility is to use a Fourier transformation for transforming the projection data sets, the spatial frequency ranges being determined by the Fourier coefficients assigned to a spatial frequency and the compensation values being determined on the basis of the Fourier coefficients.

For transforming the projection data sets per spatial frequency range, at least one filtering may likewise be carried out with a spatial frequency filter from this spatial frequency range. Decomposition of the projection data into different frequency ranges, and separate and different treatment of the data subsets resulting therefrom, is also possible by way of this. In this case, the compensation values may be determined on the basis of the pixel values of the transformation data sets.

In order to achieve noise reduction, the Inventor proposes that the calculation of temporal compensation values of the transformation data sets for a spatial frequency range should be carried out with higher-frequency spatial frequencies.

If artifact reduction is intended to be achieved for recording series in a gated CT scan of a cyclically moving or moved organ of a patient, then the calculation of temporal compensation values of the transformation data sets for a spatial frequency range may be carried out with low-frequency spatial frequencies.

In this case of the treatment of gated CT scans, absolutely chronologically successive CT projection data sets from the same motion phase or CT projection data sets which are chronologically successive in relation to motion phases may be used as a recording series.

In the first case, projection data from the same motion phase which are successive in the absolute time measurement are then considered, while in the second case the time measurement relates merely to the orientation of the motion phase.

According to at least one embodiment of the invention, average values over the entire recording sequence or moving average values over the recording sequence may be determined and used in order to calculate temporal compensation values. In general weighted sums may also be used, in which case the weight functions may have either a smoothing nature, for example trapezium functions, or a distributive nature, for example Laplace filters, or they may include a combination of the two.

The method described above may be applied both to parallel projections or fan projections.

At least one embodiment of the invention also relates to a computation unit for image processing, having a program memory, this program memory containing computer program code which carries out the method steps of the method described above during operation of the system.

At least one embodiment of the invention furthermore relates to an X-ray CT system having a control and computation unit with a program memory, this program memory also containing computer program code which carries out the method steps of the previously described method.

BRIEF DESCRIPTION OF THE DRAWINGS

The method will be described in more detail below with reference to an example embodiment with the aid of the figures. Only the features necessary for understanding the invention are represented. The references and abbreviations used here are defined as follows: 1: CT system; 2: first X-ray tube; 3: first detector; 4: second X-ray tube; 5: second detector; 6: gantry housing; 7: patient; 8: displaceable patient support; 9: system axis 10: computation and control unit; $a_{n,k}$: weight vectors; $F^{(i)}$: weight functions; f: frequency; $F_p^{(n)}$: filter in position space; G: transformation; $G^{-1}$: inverse transformation; $I_t$: image data sets of the time series, $\hat{I}_t^{(i)}$: image data sets filtered according to position frequency ranges; $\tilde{I}_t$: new image data sets of the time series; $K_p$: convolution kernel; $P(\theta,p)$: projection data sets; $Prg_1$ to $Prg_n$: computer program; $T_0$: temporal centroid; $\theta$: projection angle; $w_{t_0}^{(n)}$ projection angle-dependent weights; $\vartheta$ : : auxiliary parameter; *: convolution in direction p.

In detail:

FIG. 6 shows an example of the elimination of quickscan or subscan artifacts on lung vessels and lung tissue.

DETAILED DESCRIPTION OF THE EXAMPLE EMBODIMENTS

Figure 1:
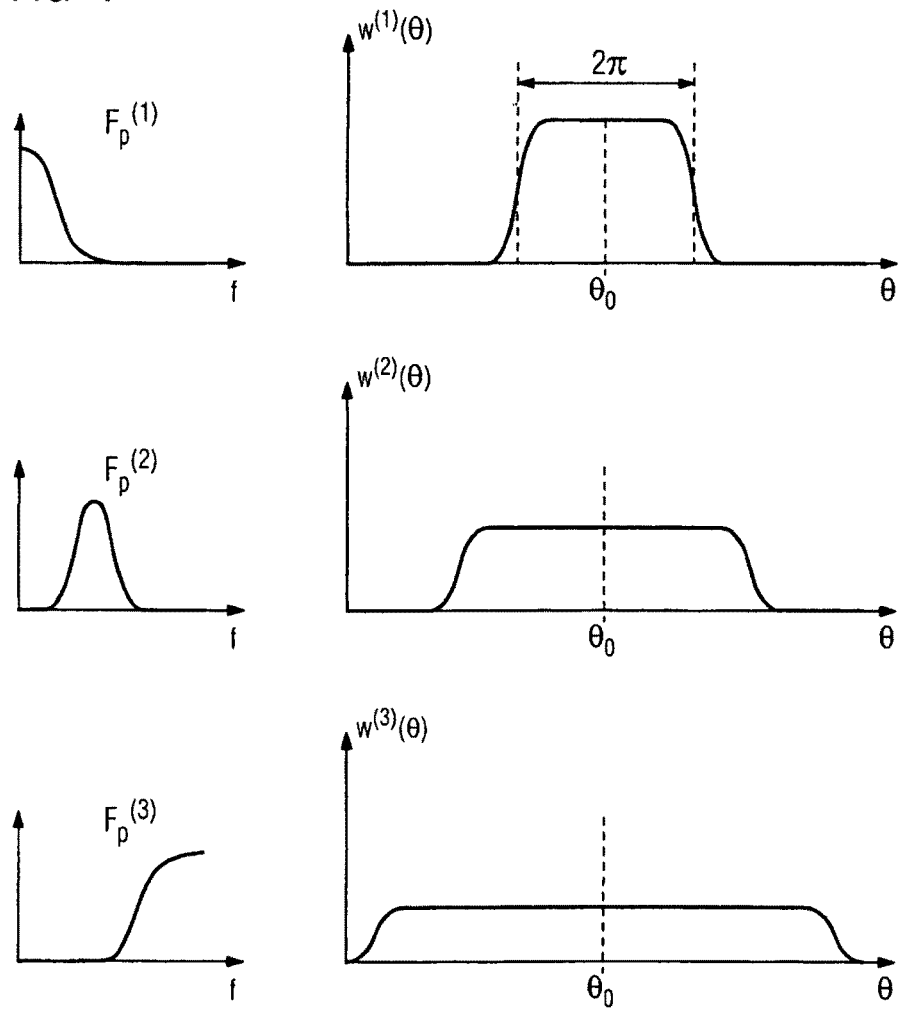
FIG. 1 shows a representation of the function of the weights $w_{T_0}^{(n)}$ for three frequency bands $F_p^{(n)}$, respectively shown on their left, for noise reduction.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/ or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The method according to an embodiment of the invention will be explained below with the aid of an example of a CT scan with a single-row detector. Of course, embodiments of the invention also comprise the generalization of the method with detectors having a plurality or multiplicity of rows.

It is to be pointed out that the dependency on the projection angle, as used, here, is to be regarded as equivalent to the time profile owing to the functional relationship between the time profile and the increment of the projection angle, which is usually linear.

First let the projection data of a multiscan, i.e. a continuously rotating scan on the position, in parallel geometry be assumed for simplicity for a tomography instrument having a detector row $P(\theta,p)$. Here, p denotes the position of the ray and $\theta$ denotes the projection angle, which extends over several rotations in CT perfusion scans. Furthermore, let $\theta_0$ be that projection angle which belongs to the instant $T_0$.

In order to calculate an image with a temporal centroid $T_0$, the following sinogram is now defined, $$P_{T_0}(\theta, p) = \sum_{n=1}^{N} w_{T_0}^{(n)}(\theta) \cdot F_p^{(n)} * K_p * P(\theta, p). \quad (1)$$

A convolution in the direction of p is denoted by "*", K denotes the convolution kernel selected by the user and $F_p^{(n)}$ denotes one-dimensional filters in position space for N frequency bands, the sum being normalized and the following being satisfied:

$$\sum_{n=1}^{N} F^{(n)}(p) = \delta_{p,0}$$

with $\delta_{p,q}=1$ if p=q and $\delta_{p,q}=0$ for p≠q. The projection angle-dependent weights $w_{T_0}^{(n)}$ must satisfy the following constraints for all frequency bands n and all projection angles $\theta$, $$\sum_{k=0,\pm1,\pm2,...} w_{T_0}^{(n)}(\theta + k \cdot \pi) = 1. \quad (2)$$

In order to fix the temporal centroid at $T_0$, the following must furthermore apply in each frequency band n $$\sum_{\vartheta} (\theta_0 - \vartheta) \cdot w_{T_0}^{(n)}(\theta_0 - \vartheta) = 0, \quad (3)$$

where $\vartheta$ ranges over all projection, angles. Advantageously, $w_{T_0}^{(n)}$ may be selected symmetrically, $$w_{T_0}^{(n)}(\theta_0 + \vartheta) = w_{T_0}^{(n)}(\theta_0 - \vartheta), \quad (4)$$

so that Condition (3) is satisfied automatically. If no projections $P(\theta,p)$ are available for calculating $P_{T_0}(\theta,p)$ at the scan start or scan end, then these may for example be replaced by the closest possible projections or complementary projections, $P(\theta \pm k \cdot \pi, p)$, for a suitable natural number k. The projection data $P_{T_0}(\theta,P)$ determined as above are subsequently projected back, preferably unfiltered, in order to obtain the image $\tilde{I}_{T_0}$.

When this embodiment of the method is applied for noise reconstruction reduction in CT perfusion measurements, then the temporal width of $w_{T_0}^{(1)}$, or the projection angle width, is narrow and that of $w_{T_0}^{(N)}$ is to be selected wider if frequency band 1 contains the low frequencies and band N contains the highest frequencies. A typical example for selection of the weights is represented in FIG. 1 for three frequency bands. Here, the three frequency bands $F_p^{(i)}$ are respectively represented graphically by their transfer functions in frequency space on the left, and the profile of the associated weights $W_{T_0}^{(i)}$ as a function of the projection angle $\theta$ is represented on their right. In accordance with the requirement for noise reduction, wide weight functions for high spatial frequencies and narrow weight functions for low spatial frequencies are used here in projection space.

Figure 2:
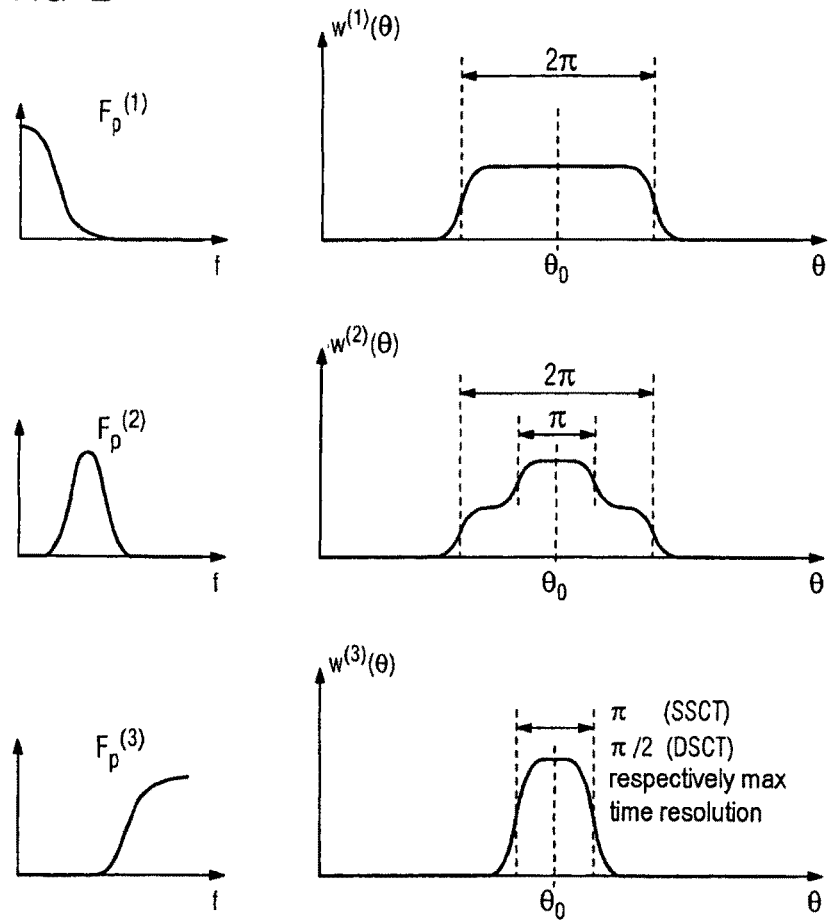
FIG. 2 shows a representation of the function of the weights $w_{T_0}^{(n)}$ for three frequency bands $F_p^{(n)}$, respectively shown on their left, for subscan artifact reduction in gated CT scans.

For artifact reduction in gated CT scans, the widths are to be selected in precisely the opposite way as a function of the frequency bands. A corresponding representation is shown in FIG. 2.

In both variants, the weight functions advantageously contain "soft" transitions regions at the edges, for example $\cos^2$ windows, in order to suppress artifacts at the junctions.

The method according to an embodiment of the invention is thus not restricted to parallel projections, and may likewise be applied to projection data in fan geometry, $P(\alpha,\beta)$. This is done, for example, by prior rebinning of fan data to parallel data, or a direct treatment; in the latter case the kernel $K_\beta$ must be selected as a kernel in fan geometry and the weighting, including normalization, must also be channel-dependent i.e. dependent on $\beta$, so that weights $w_{T_0}^{(n)}(\alpha, \beta)$ have to be used.

In a spiral scan, no planar raw data are initially available. Here, in a first step, reinterpolation to 2D planar data may initially be carried out with the aid of a spiral interpolation as is customary for all 2D spiral reconstructions.

In 3D-filtered backprojection algorithms, the components of the n bands, $$P_{T_0}^{(n)}(\theta,p) = w_{T_0}^{(n)}(\theta) \cdot F_p^{(n)} * K_p * P(\theta,p) \quad (5)$$

are projected back separately. In order to obtain the desired noise or artifact reduction effect, it is necessary to ensure that each voxel sees rays from an angle segment with the maximum window width of the functions $w_{T_0}^{(n)}$, which limits the maximum possible table forward increment.

The approach in respect of the method carried out at the data level as formulated above for noise reduction, when using Fourier transformations and isotropic filters for G, is mathematically a special case of the method proposed according to an embodiment of the invention, although in the latter case the filtering for decomposition into bands takes place at a point in the image reconstruction which has to be filtered with a regular CT convolution kernel anyway. Since the convolution is conventionally carried out equivalently as multiplication in frequency space, the extra cost thus includes only of a further multiplication by the frequency representation of the functions $F_p^{(n)}$ and a weighted sum according to Formula (I).

Figure 3:
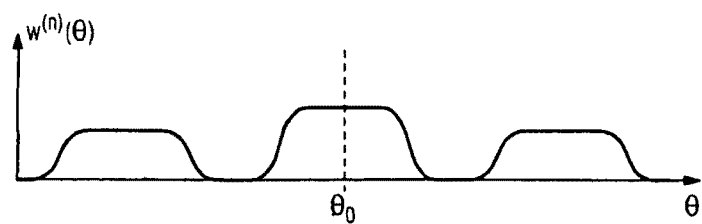
FIG. 3 shows a representation of the function of the weights $w_{T_0}^{(n)}$ for noise reduction in a zigzag spiral scan.

The method according to an embodiment of the invention may also be used in conjunction with zigzag spirals for dynamic CTAs or perfusion CT. It should be noted here that the voxels are scanned not continuously but with temporal gaps in a zigzag scan. This is to be taken into account for the weighting functions of the bands. FIG. 3 shows by way of example the profile of a weighting factor $w_{T_0}^{(n)}$ as a function of the projection angle θ for such a zigzag spiral scan, in which case Conditions (2) and (3) furthermore need to be satisfied.

Figure 4:
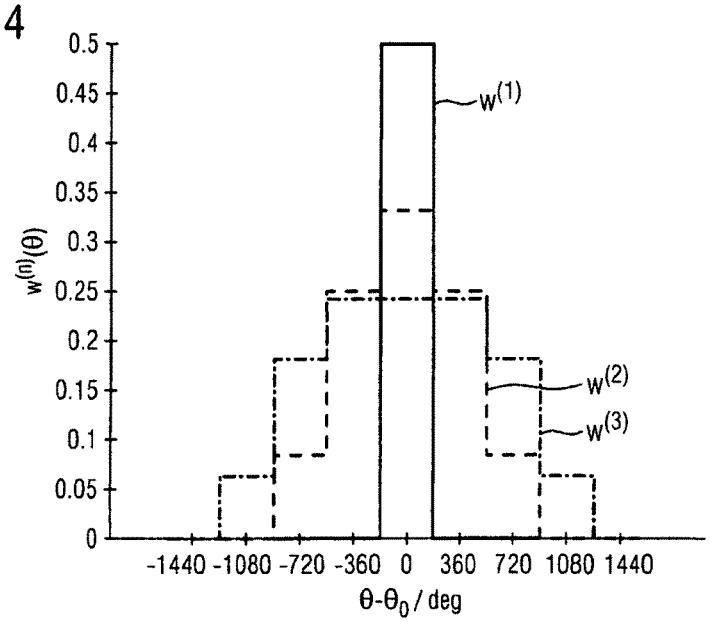
FIG. 4 shows three weight functions as a function of the projection angle $\theta$ in three different frequency ranges N=1 to 3 for the case of noise suppression.

FIG. 4 shows an advantageous example of the profile of three weight functions as a function of the projection angle θ for three different frequency ranges N=1 to 3 for the case of noise suppression. In accordance with the comments above, the weight functions proceed very narrowly in the lowest frequency band N=1, somewhat more broadly in the middle frequency band N=2, and most broadly in the highest frequency band.

Figure 5:
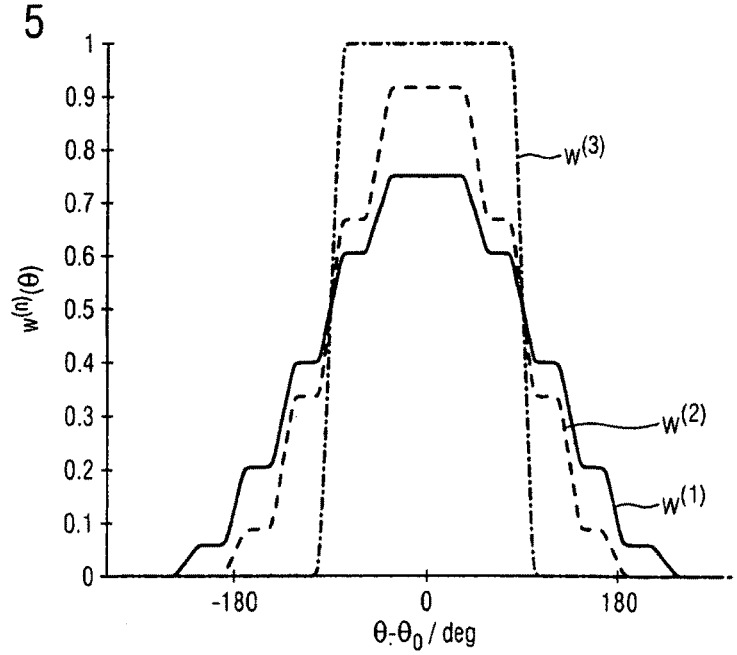
FIG. 5 shows three weight functions as a function of the projection angle $\theta$ in three different frequency ranges N=1 to 3 for the case of artifact reduction in gated CT scans.

Another example for the case of a gated CT scan is shown in FIG. 5. Here, the profile of the weight functions is selected in the opposite way. The broader profile of the weight functions is assigned to the lower frequency band, and the narrower profile to the higher frequency band. Furthermore, the transitions here—in contrast to FIG. 4—are not stepped but somewhat smoothed, so that possible transition artifacts are avoided.

In contrast to the similar methods mentioned above based on the already reconstructed image data in approaches used in the cited prior art, the method according to an embodiment of the invention entails a much lower computation cost as shown in the following table for N=3.

|  | Cost per image when applied to image data | Cost per image when applied to projection data |
|---|---|---|
| Perfusion CT | 1 reconstr. + 2 × 2D FFTs ≅ 2 reconstructions | 1 reconstruction |
| Gated reconstruction 3D FBP | 5-7 reconstr. + 10-14 2D FFTs ≅ 10-14 reconstr. | 3 reconstructions |

In particular for application in gated cardio CTs, better functions can be constructed with the method according to an embodiment of the invention and the calculation can be accelerated significantly.

FIG. 6 shows an example of the elimination of quickscan or subscan artifacts on lung vessels and lung tissue. In FIG. 6, an original recording without application of the method according to an embodiment of the invention is shown at the top left, and the same recording comprising projection data processed according to an embodiment of the invention is shown on its right. A differential image between the original image and the image comprising filtered data is shown at the bottom left. The weight functions used for 3 frequency bands are represented at the bottom right.

It should be pointed out that the method according to an embodiment of the invention may be employed for all CT scans in which time series of the same subject are sampled. In particular, the method may also be applied to scans with different X-ray energies, in which case it may be employed both for noise suppression in simple CT scans and for subscan artifact suppression of gated dual- or multi-energy scans.

Figure 7:
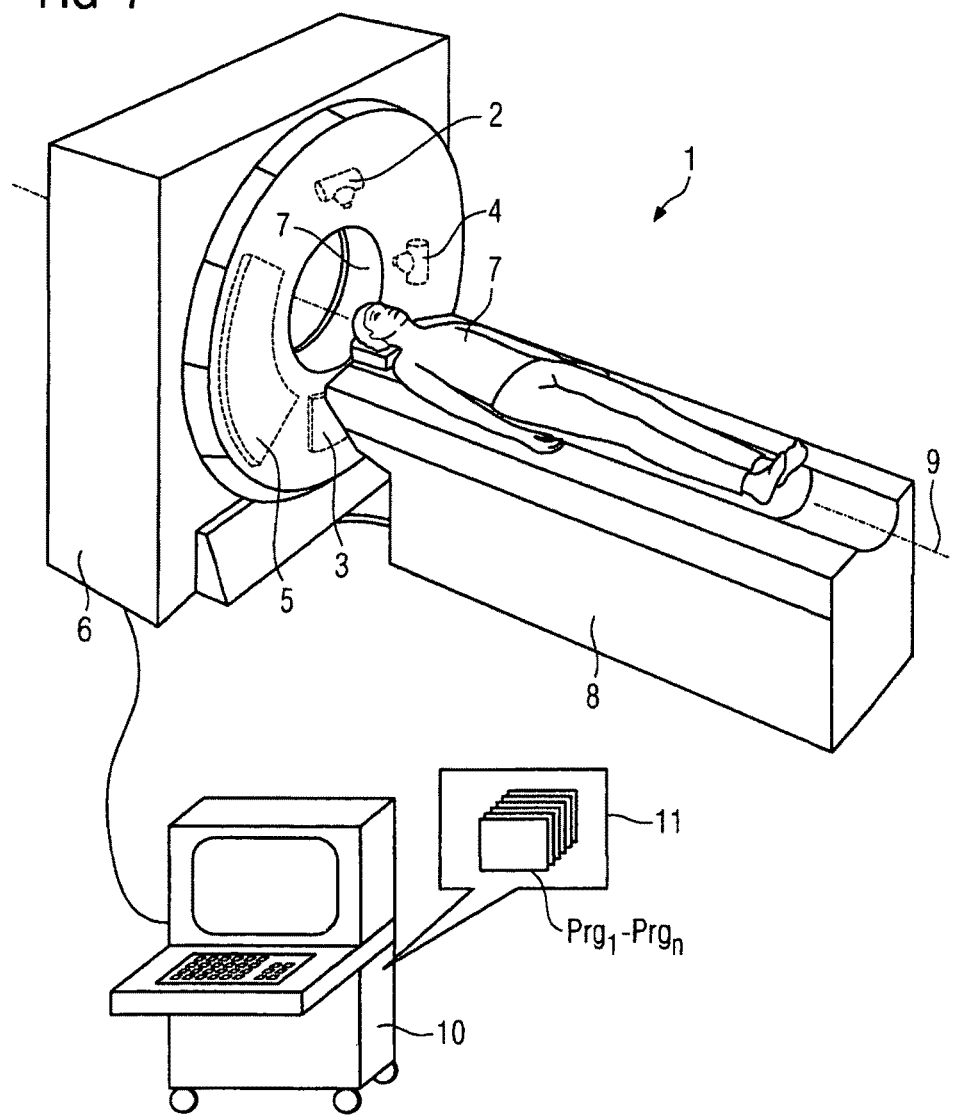
FIG. 7 shows a CT system for carrying out the method according to an embodiment of the invention.

For example, FIG. 7 represents a CT system 1 which is suitable for carrying out the method according to an embodiment of the invention. This CT system includes of a gantry housing 6 having a first beam/detector system, including a first X-ray tube 2 and a first detector 3 lying opposite, arranged on the gantry (not represented in detail). Further beam/detector systems may optionally be provided, such as the second beam/detector shown here by way of example with a second X-ray tube 4 and a second detector 5 lying opposite. Such multiple beam/detector systems may be used on the one hand to improve the time resolution when using the same X-ray spectra, and also to improve the resolution of tissue differences when using different X-ray spectra.

The patient 7 lies on a displaceable patient support 8, so that he or she can be moved in a continuous or sequential fashion during the CT scan along the system axis 9 through the measurement field of the CT system 1 a forward and backward movement may likewise be carried out during the scan, so that a zigzag spiral is executed. The method according to the invention may by way of example be run on the control and computation unit 10, the schematically represented memory 11 storing computer programs $Prg_1$ to $Prg_n$ which inter alia, i.e. besides controlling the system and the subsequent image reconstruction, carry out the method described in this application during operation.

It is to be understood that the features of the invention as mentioned above may be used not only in the combination respectively indicated, but also in other combinations or in isolation, without departing from the scope of the present invention.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for increasing quality of computer tomographic recording series, the method comprising:
scanning a subject over a period of time to record at least two temporally offset projection data sets of the same recording region;
transforming the projection data sets into transformation data sets for at least two spatial frequency ranges;
calculating temporal compensation values of the transformation data sets for some of the spatial frequency ranges and replacing values of the transformation data sets with the calculated compensation values in new transformation data sets, wherein projection data of congruent rays is always compared;
transforming the new transformation data sets back into new projection data sets;
reconstructing image data sets on the basis of the transformed new projection data sets; and
representing the reconstructed image data sets.

2. The method as claimed in claim 1, wherein a wavelet transformation is used for transforming the projection data sets.

3. The method as claimed in claim 2, wherein the spatial frequency ranges are determined by the level of the wavelet transformation.

4. The method as claimed in claim 3, wherein the compensation values are determined on the basis of the wavelets.

5. The method as claimed in claim 2, wherein, for artifact reduction of a recording series in a gated Computed Tomography (CT) scan of a cyclically moving or moved organ of a patient, the calculation of temporal compensation values of the transformation data sets for a spatial frequency range is carried out with low-frequency spatial frequencies.

6. The method as claimed in claim 1, wherein, for transforming the projection data sets for at least one spatial frequency range each, at least one filtering is carried out with a spatial frequency filter from this spatial frequency range.

7. The method as claimed in claim 6, wherein the compensation values are determined on the basis of the pixel values of the transformation data sets.

8. The method as claimed in claim 1, wherein, for noise reduction, the calculation of temporal compensation values of the transformation data sets for a spatial frequency range is carried out with higher-frequency spatial frequencies.

9. The method as claimed in claim 1, wherein, for artifact reduction of a recording series in a gated Computed Tomography (CT) scan of a cyclically moving or moved organ of a patient, the calculation of temporal compensation values of the transformation data sets for a spatial frequency range is carried out with low-frequency spatial frequencies.

10. The method as claimed in claim 9, wherein chronologically successive CT projection data sets from the same motion phase are used as a recording series.

11. The method as claimed in claim 9, wherein CT projection data sets which are chronologically successive in relation to motion phases are used as a recording series.

12. The method as claimed in claim 1, wherein average values are determined over the entire recording sequence and used in order to calculate temporal compensation values.

13. The method as claimed in claim 1, wherein moving average values are determined over the recording sequence and used in order to calculate temporal compensation values.

14. The method as claimed in claim 1, wherein the method is applied to fan projections with comparison respectively of an equal projection direction.

15. A non-transitory computer readable medium storing computer code that, when executed by a processor executes the method of claim 1 during operation of the computation unit.

16. An X-ray Computed Tomography (CT) system comprising:
a controller and a non-transitory computer readable medium storing computer code that, when executed by the controller executes the method of claim 1 during operation of the X-ray system.

17. An image processing apparatus, comprising:
means for scanning a subject over a period of time which makes it possible to record at least two temporally offset projection data sets of the same recording region;
means for transforming the projection data sets into transformation data sets for at least two spatial frequency ranges;
means for calculating temporal compensation values of the transformation data sets for some of the spatial frequency ranges and replacing values of the transformation data sets with the calculated compensation values in new transformation data sets, wherein projection data of congruent rays is always compared;
means for transforming the new transformation data sets back into new projection data sets;
means for reconstructing image data sets on the basis of the transformed new projection data sets; and
means for representing the reconstructed image data sets.

18. An X-ray Computed Tomography (CT) system comprising the apparatus of claim 17 and further comprising means for controlling the X-ray CT system.

* * * * *